United States Patent [19]

Evans et al.

[11] 4,216,498
[45] Aug. 5, 1980

[54] VISIBILITY MONITOR EMPLOYING TELEVISION CAMERA

[75] Inventors: William E. Evans, Los Altos Hills; William Viezee, Palo Alto, both of Calif.

[73] Assignee: SRI International, Menlo Park, Calif.

[21] Appl. No.: 941,688

[22] Filed: Sep. 12, 1978

[51] Int. Cl.² .................. H04N 5/30; H04N 7/02
[52] U.S. Cl. .................. 358/93; 356/222; 356/435; 358/107; 358/209; 358/903
[58] Field of Search .......... 358/93, 903, 107, 209, 358/125, 126, 105, 219; 356/433, 434, 435, 218, 219, 222

[56] References Cited

U.S. PATENT DOCUMENTS

| 3,329,821 | 7/1967 | Lesage | 356/435 |
| 3,812,483 | 5/1974 | Graves | 358/105 |

*Primary Examiner*—Robert L. Richardson
*Attorney, Agent, or Firm*—Victor R. Beckman

[57] ABSTRACT

Visibility monitoring method and means are disclosed employing a video camera for monitoring an area which includes a low reflectance (substantially non-reflecting) target at known range from the camera and adjacent horizon sky. Window gating circuit means under control of a programmable digital computer are used to gate selected portions of the output from the video camera to integrating means for generating signals related to brightness of at least a portion of the target and adjacent horizon sky. The brightness related signals are supplied to said digital computer for use in computing visual contrast, visibility, or the like. Preferably, a plurality of substantially non-reflecting targets at different ranges are employed for increased accuracy.

17 Claims, 5 Drawing Figures

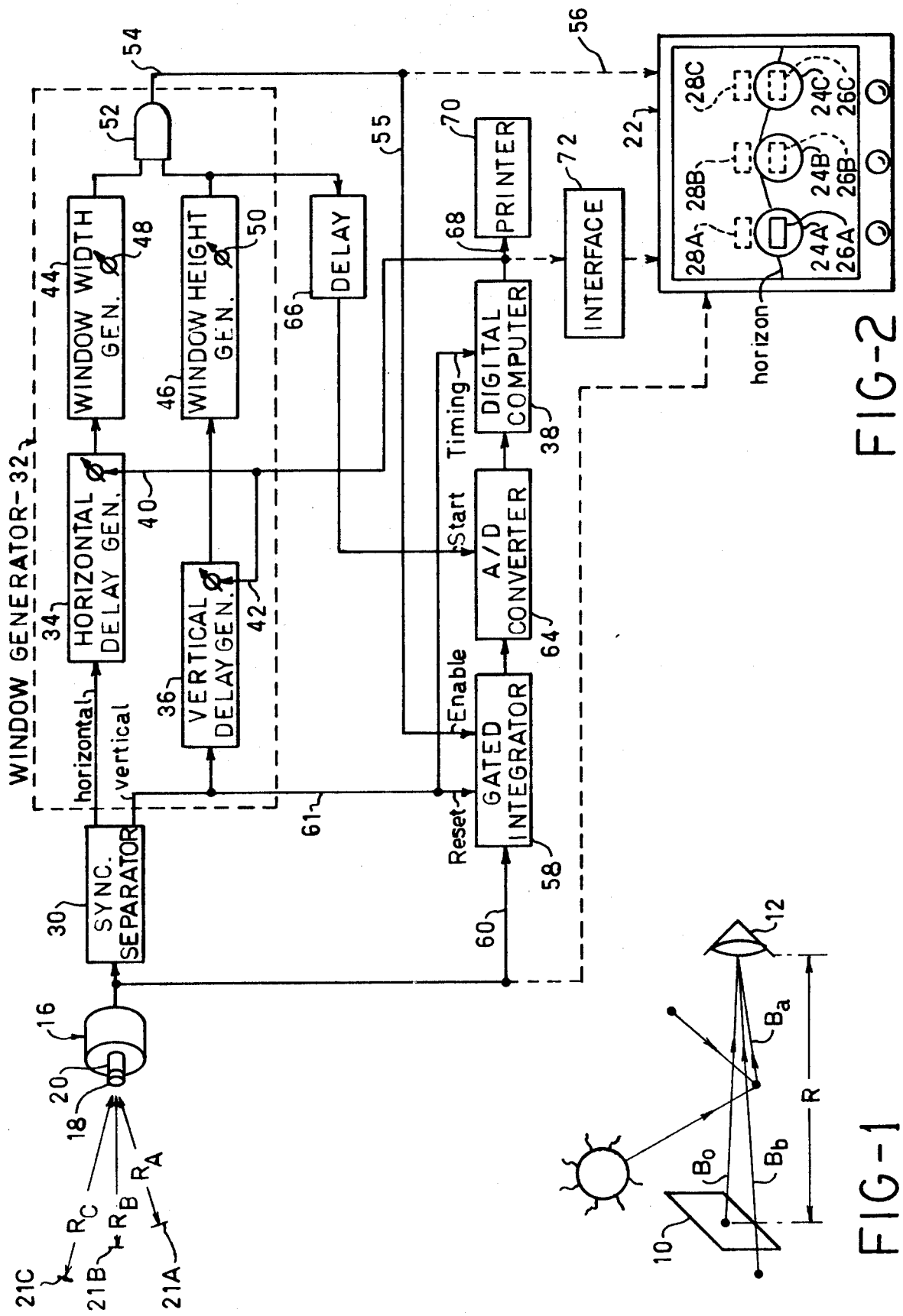

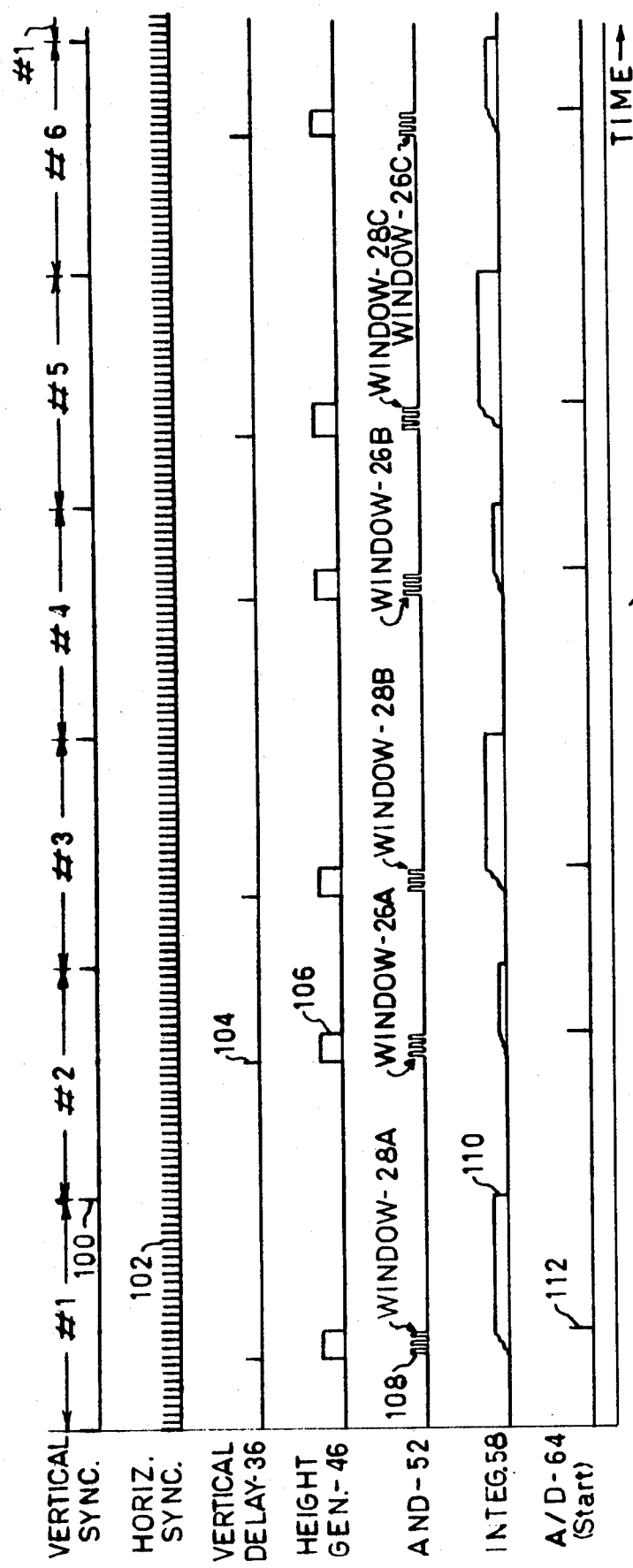
FIG-3
FIG-4
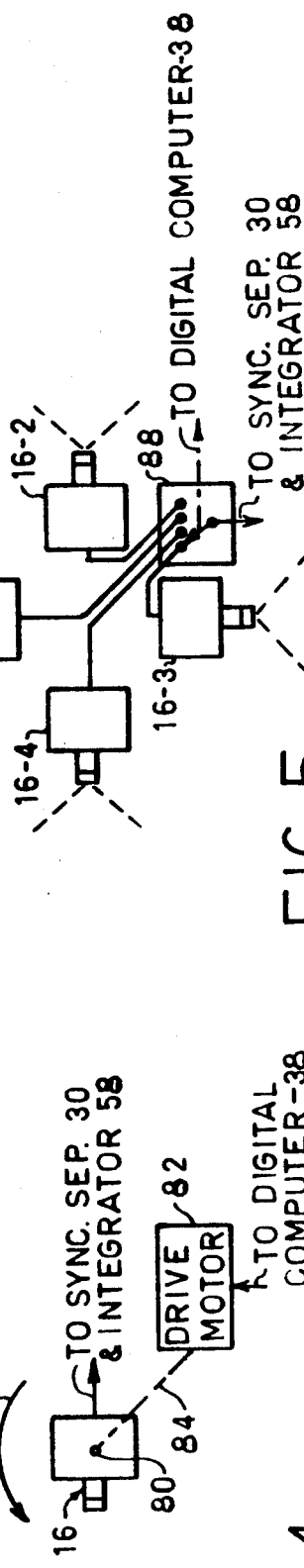
FIG-5

VISIBILITY MONITOR EMPLOYING TELEVISION CAMERA

BACKGROUND OF THE INVENTION

Visibility may be measured in terms of the amount of visible radiation propagated through the atmosphere from distant objects, and the present invention involves the use of such measurements. Daytime visibility, in general, refers to the greatest distance in a given direction at which it is just possible to see and identify a prominent dark object against the sky at the horizon with the unaided eye. If such visibility measurements are made around the entire horizon, they may be resolved, or combined, into a single value of prevailing visibility, which is the greatest horizontal visibility equalled or surpassed throughout half of the horizon circle.

Heretofore, telephotometers have been used for making measurements of visual range in the atmosphere. However, a major disadvantage in the use of such instruments is that a human operator must be present to make the necessary measurements. As a result, continuous measurements of visibility are not practical using such instruments.

SUMMARY OF THE INVENTION

An object of this invention is the provision of improved method and means for making visual brightness measurements of distant objects for use in determining brightness contrast between adjacent target areas, visibility, and/or prevailing visibility of the atmosphere.

An object of this invention is the provision of improved brightness measuring method and apparatus for use with distant targets from which continuous brightness contrast, visibility, prevailing visibility, or the like measurements may be made without the need for a human operator.

An object of this invention is the provision of brightness measuring method and apparatus readily adapted for continuously and accurately monitoring of visibility over a wide range of visibilities.

The above and other objects and advantages of this invention are achieved by use of one or more video cameras directed at appropriate distant targets together with suitable circuitry, including a programmable digital computer, for sampling the video signal at selected target areas and for automatically converting the sampled signals to visual brightness contrast and/or visibility measurements on a continuous basis. One or more preselected substantially non-reflecting targets are included within the viewing field of the camera, which targets may comprise landmarks or dedicated targets, and which targets may be located at different distances from the camera for improved accuracy of the visibility determinations. If desired, a plurality of cameras together with suitable targets may be included for obtaining visual brightness contrast readings from around substantially the entire horizon, from which readings a single prevailing visibility value may be calculated by the computer. Alternatively, a single camera which is movably mounted for scanning the entire horizon may be used, with movement under computer control.

BRIEF DESCRIPTION OF THE DRAWINGS

The invention, together with further objects and advantages thereof, will be better understood from the following description considered with the accompanying drawings. In the drawings, wherein like reference characters refer to the same parts in the several views:

FIG. 1 is a diagram illustrating contrast reduction from atmospheric scattering and absorption;

FIG. 2 is a block diagram showing a visibility monitoring system embodying the present invention;

FIG. 3 is a timing diagram to facilitate description of the operation of the novel visibility monitoring system;

FIG. 4 is a plan view of a rotatably mounted camera useable with this invention for scanning around the entire horizon; and FIG. 5 is a fragmentary block diagram of a visibility monitoring system employing a plurality of cameras for viewing substantially the entire horizon.

DETAILED DESCRIPTION

Before describing the visibility monitoring system of this invention in detail, a brief description of principles involved in measuring visual brightness contrast and visibility will be provided. In several nations, including the United States of America, daytime visibility is defined as the greatest distance in a given direction at which it is possible to see and identify with the unaided eye a prominent dark object against the sky at the horizon. Prevailing visibility is obtained by measuring visibilities around the entire horizon, and then determining the greatest horizontal visibility equalled or surpassed through half, but not necessarily a continuous half, of the horizon circle. As noted above, a telephotometer commonly has been employed for making brightness measurements of substantially non-reflecting targets and background horizon sky from which visibility may be determined.

In FIG. 1, to which reference now is made, a diagram illustrating contrast reduction as a result of atmospheric scattering and absorption is shown wherein $B_o$ and $B_b$ are defined as the brightness, i.e., visual luminance, of a remote object 10 and its background when viewed from the direction of an observer 12. The inherent visual brightness contrast of the object with respect to its background is defined as the ratio $$C = \frac{B_o - B_b}{B_b} \quad (1)$$

which, in turn, is the fundamental measure of the discernability of the object to the human eye. Attenuation by atmospheric particles and gases along the viewing path reduces $B_o$ and $B_b$ to the values $T(R)B_o$ and $T(R)B_b$, respectively, where $T(R)$ is the atmospheric transmittance of the path between the observer, at range 0, and the viewed object, at the viewing range R. At the same time, atmospheric particles and gases along the path scatter sunlight and skylight into the eye of the observer, thereby producing an apparent brightness $B_a$ frequently referred to as the "airlight." The combined result of attenuation and airlight yields the following apparent brightness coming from the object and its background, respectively.

$$B_o' = T(R)B_o + B_a \quad (2a)$$

$$B_b' = T(R)B_b + B_a \quad (2b)$$

which result in the following apparent contrast of the object, at range R, with respect to its background, as perceived by the observer at range 0:

$$C' = \frac{B'_o - B'_b}{B'_b} \quad (3)$$

Using equation (1), (2a) and (2b), equation (3) becomes $$C' = C \frac{B_b}{B'_b} T(R) \quad (4)$$

and this is the most general expression for the law of contrast reduction by the atmosphere.

In principle, it is possible to determine daytime visibility referenced to a fixed location by remotely measuring the visual brightness contrast of distant dedicated targets by means of photometry. A simplified procedure can be developed as follows. For a distant ground-based target viewed in a horizontal direction against the horizon sky, equation (4), above, can be rewritten as $$C' = C \frac{B_h}{B'_h} \exp(-\bar{\sigma} R) \quad (5)$$

where $B_h$ = horizon sky brightness as seen at the target location;

$B'_h$ = horizon sky brightness as seen at the observation location;

R = distance between viewed target and observer, and $\bar{\sigma}$ = average atmospheric extinction coefficient over distance R.

By assuming constant atmospheric extinction and airlight per unit length in an infinite horizontal plane, the horizon sky brightness is the same at the observer as it is at the viewed target, i.e. $B'_h = B_h$ and, therefore, $$\frac{C'}{C} = \frac{B'_o - B_h}{B_o - B_h} = \exp(-\bar{\sigma} R) \quad (6)$$

where $B_o'$ = apparent target brightness measured at distance R, $B_o$ = intrinsic target brightness, and $B_h'$ = horizon sky brightness measured at distance R.

Quantitive measurements of $B_o'$ and $B_h'$ may be obtained with the aid of a telephotometer located at a predetermined distance R with respect to the viewed target. For a poorly reflecting target, $B_o$ can be obtained by calibrating the target under "pure air" conditions. Distance R may be obtained, for example, from a map or by direct measurement. For an ideal black target, i.e. $B_o = 0$, C = 1 and $$C' = \frac{B'_o - B_h}{B'_h} = \exp(-\bar{\sigma} R) \quad (7)$$

Knowing R, $\bar{\sigma}$ can be determined by measuring $B_o'$ and $B_h'$. Visual range V can then be computed from Koschmieder's law, using the relationship:

$$C' = \exp(-\bar{\sigma} R) = \exp\left(-\frac{2.9R}{V}\right) \quad (8)$$

for a lower threshold of visual contrast equal to 0.055.

Rearranging equation (8) provides an equation for visual range $$V = \frac{-2.9R}{\ln C'} \quad (9)$$

Using equation (7) in equation (9), the equation for visual range in terms of known distance R, measurable target brightness $B_o'$, and horizon sky brightness $B_h'$ at the distance R becomes $$V = \frac{-2.9R}{\ln\left(\frac{B'_o - B'_h}{B'_h}\right)} \quad (10)$$

Reference now is made to FIG. 2 wherein a simplified block diagram of a visibility monitoring system which embodies the present invention is shown comprising a television camera 16, an optical filter combination 18 to provide a camera spectral response substantially corresponding to that of the human eye, and a long focal length lens 20 for viewing distant targets, such as substantially non-reflecting targets 21A, 21B and 21C positioned at ranges $R_A$, $R_B$ and $R_C$, respectively, from the camera. For operation over extended periods, without the need for continual operator calibration, a camera having a stable and highly linear brightness transfer characteristic is desired. Silicon-target type vidicon cameras having such properties are well known and may be employed in the present monitoring system. Of course, conventional vidicon type television cameras may be employed if means for calibrating the tube response over a wide range of faceplate illumination levels are included. Such means, however, greatly complicate quantitative measurements. Consequently, the use of a silicon-target type camera having a stable and linear brightness transfer characteristic in the visibility monitoring system is desirable. Other types of television cameras are known which may be used in the present system including, for example, solid state array cameras which are physically rugged and have a fixed, non-alterable, scan geometry. Presently, however, other performance characteristics, such as resolution and target uniformity of these cameras generally do not match those of the silicon-target type vidicon, and further development is desirable.

For purposes of illustration, and to facilitate explanation of the invention, the composite video output signal from the television camera 16 is shown supplied to a video monitor 22 where the camera scene is displayed along with a cursor for identifying areas of the scene sampled for visual luminance. The monitor is useful in setting up the system for identifying those portions of the scene which are to be sampled for visual luminance. However, as will become apparent herein below, during operation of the system, the use of the monitor is not required and the monitor may be excluded from the operating system.

As mentioned above, substantially non-reflecting targets 21A, 21B and 21C are shown within viewing range of the camera and the corresponding target images 24A, 24B and 24C, respectively, are shown at the monitor screen. The targets are located at different azimuthal locations and may, if desired, be located at different distances from the camera at, say 1, 5 and 9 miles, respectively, therefrom. The use of three targets and the abovementioned distances simply are for purposes of illustration, the invention not being limited to such number or such distances. Also, either dedicated targets or suitable landmarks may be employed. As seen at the screen of the monitor, cursor 26A is positioned at the target image 24A for visual luminance measurement thereof. The cursor also is positionable, under computer control, at locations 26B and 26C, shown in broken lines, at the target images 24B and 24C, respectively, for visual luminance measurements of such targets. For visual brightness contrast and visibility determinations, horizon sky brightness measurements adjacent said targets may be employed. To this end the cursor, under computer control, is positionable at locations 28A, 28B and 28C at the horizon sky adjacent the target images 24A, 24B and 24C, respectively.

With the system of this invention, the composite video signal output from the television camera 16 is supplied to a synchronizing signal separator (sync. separator) 30 which may be of conventional design, for separation of the horizontal and vertical synchronizing signals from the video signal portion and from each other. The horizontal and vertical synchronizing signals are supplied as inputs to a programmable window generator 32 for use in generating the above-mentioned cursors and corresponding camera windows during which the video signal is passed to the remainder of the monitor circuit for processing in accordance with this invention.

The programmable window generator 32, which may be of substantially conventional design, includes horizontal and vertical delay generators 34 and 36, respectively, to which the respective horizontal and vertical synchronizing signals are supplied to trigger the same. The delay generators simply may comprise monostable multivibrators which generate an output pulse of adjustable duration; the duration of which pulses is under control of outputs from a digital computer 38 connected thereto over channels 40 and 42, respectively. Preferably, however, the delay generators comprise clocked digital circuits, such as programmable counters, or the like, from which an output pulse is provided after a delay time following receipt of an input pulse; with the delay time being under control of outputs from the digital computer 38. In any event, delays provided by the generators 36 and 34 serve to position the cursor and camera window.

Outputs from the horizontal and vertical delay generators 34 and 36 are supplied to pulse width generators 44 and 46, respectively, to trigger the same. Again, the pulse width generators simply may comprise monostable multivibrators which, when triggered, provide an output pulse having a width set by adjustable control means 48 and 50, respectively, with adjustment of the control means 48 and 50 serving to set the respective width and height of the illustrated cursor and camera window during video signal processing. Alternatively, the pulse width generators may comprise programmable counters, or like clocked digital circuits, and associated circuitry from which an output pulse may be derived when triggered by the outputs from the horizontal and vertical delay generators 34 and 36, respectively. If desired, such generators too could be controlled by digital computer 38 outputs for computer control of the size of the window gates and cursor to better fit individual target sizes. Generally, the same window size is employed for a target and associated horizon sky measurement (e.g. cursors 26A and 28A generally would be of equal size, as would cursors 26B and 28B, and cursors 26C and 28C) for brilliance measurements over corresponding size areas of the scene. If different window sizes for adjacent targets (e.g. a target and associated horizong sky area) are employed, the computer 38 simply is programmed to accomodate the size difference in computations performed on the brightness related signals obtained therefrom.

Finally, the window generator 32 is shown to include an AND gate 52 to which pulse outputs from window width and height generators 44 and 46, respectively, are supplied. With this arrangement, pulses from the window width generator 44 effectively are gated to the output from the window generator only during the presence of an output pulse from the window height generator 46. The window height generator 46 essentially establishes which horizontal scan lines may be passed to the window generator output, while the window width generator 44 establishes what portion of the selected horizontal scan lines is passed.

The window gate pulses at line 54 from AND gate 52 are shown supplied over line 56 to the video monitor through a suitable interface of conventional design, not shown, for cursor display. The windows 26A, 26B and 26C for the targets 21A, 21B and 21C are adjusted for position and size to fall within the target images 24A, 24B and 24C, respectively. In the illustrated arrangement the windows 26A, 26B and 26C for target brightness measurements are shown of equal size and of the same size as windows 28A, 28B and 28C for associated horizon sky brightness measurements. As noted above, the window positions are established by outputs from programmable digital computer 38 properly programmed to provide such outputs at the appropriate times. Also, as noted above, different target window sizes may be employed, if desired, with the window size being under control of digital computer 38 by use of computer outputs supplied to the window width and height generators 44 and 46 for control of the pulse width outputs therefrom.

The video signal output from the camera 16 is supplied as an input to a gated integrator 58 over line 60. The integrator is enabled, i.e. gated on, by the output from the window generator 32 connected thereto over lines 54 and 55 from the AND gate 52 and, in the illustrated arrangement, is reset by use of the vertical synchronizing signal supplied thereto as a reset control signal over line 61 from the synchronizing signal separator 30. (It here will be noted that the vertical synchronizing signal also is supplied to the computer 38 for timing purposes). The video signal present at the input to the integrator 58 during the time that the integrator is enabled by a window gate thereby is integrated to provide an output from the integrator which corresponds to the visual brightness of the area identified by the window; here, either a low-reflectance target or associated horizon sky background.

After each window, the analog visual brightness signal from the integrator 58 is converted to digital form by use of an analog-to-digital converter 64, the output from which converter is supplied to the digital computer 38 for any desired use, including use in calculating the visual brightness difference and/or visual brightness contrast between a low-reflectance target and the adjacent horizon sky. Also, visibility in the direction of a visible target may be calculated using equation (10) above. Analog to digital conversion is initiated by a signal from a delay unit 66 triggered by the trailing edge of the window height pulse from window height generator 46. As noted above, the range, or distance, to the targets from the camera is known, having been obtained from a map, by direct measurement, or the like, and this information is supplied to the computer for use in performing visibility calculations from the visual brightness measurements. Where additional brightness information is obtained from additional targets and associated horizon sky backgrounds, further processing of the additional measurements by the computer is obvious to provide other visibility related outputs such as prevailing visibility. Programming of the digital computer 38 to perform such calculations from the range and brightness information supplied thereto, and for setting the delays for the horizontal and vertical delay generators 34 and 36 for positioning the window, is well within the capabilities of one skilled in the present art and requires no further description. (Similarly, programming for setting the width of the pulse outputs from the window width and height generators 44 and 46, where such generators are digitally controlled, or programmed, is well within the skill of the artisan.) In the illustrated arrangement brightness, brightness difference, brightness contrast and/or visibility measurements and calculations from the computer are connected over line 68 to a printer 70 to provide a permanent record thereof. Such a printed record may be provided at predetermined time intervals and/or when the measurements or calculations change a predetermined amount under changing visibility conditions. Also, this information may be displayed at the video monitor by connection to the monitor through a suitable interface 72 which includes a character generator.

Although the operation of the monitoring system and method of the present invention is believed to be apparent from the above description, a brief description thereof with reference to the timing diagram of FIG. 3 now will be made. Vertical and horizontal synchronizing signals (waveforms 100 and 102, respectively) produced by the television camera 16 and separated by synchronizing signal separator 30 are supplied to the vertical and horizontal delay generators 36 and 34, respectively, of window generator 32 to trigger the same. The outputs from the horizontal and vertical delay generators change state after time delay periods set by outputs from the computer 38 supplied to the delay generators over channels 40 and 42, respectively. For simplicity, only the output 104 from the vertical delay generator 36 is shown in FIG. 3, it being understood that a horizontal delay generator output pulse also is produced by the horizontal delay generator 34 for each horizontal synchronizing signal input supplied thereto. These adjustably delayed window positioning pulses from horizontal and vertical delay generators 34 and 36 serve to trigger the window width and height pulse generators 44 and 46, respectively, and, in the illustrated arrangement, adjustable controls 48 and 50 are used to set the window width and height, respectively. In the timing diagram of FIG. 3, the window height generator 46 output 106 is shown together with only those window width generator output pulses 108 which occur during generator 46 output 106. It will be seen, then, that waveform 108 comprises the output from AND gate 52 from the window gate generator 32.

The window gating pulses 108 from window gate generator 32 enable the gated integrator 58 for integration of the video signal output from the camera 16 during such times. For purposes of clarity, relatively few of the total number of horizontal synchronizing signal pulses 102 are shown in FIG. 3, such that each window is shown as comprising only three pulses from window width generator 44. In practice the window generally would include portions of more than three horizontal scan lines of information. When the analog signal output 110 from the gated integrator 58 stabilizes following a window gate, conversion to digital form by the analog to digital converter 64 is effected. Waveform 112 identifies a timing pulse from delay unit 66 derived from the trailing edge of pulse 106 from generator 46 for initiating the analog to digital conversion.

As seen in FIG. 3, during fields #1 and #2, visual brightness values for windows 28A and 26A are obtained (from which visual brightness difference, visual brightness contrast and/or visibility of target 24A may be calculated using the computer). Similarly, visual brightness difference, visual brightness contrast, and/or visibility of targets 24B and 24C are computed following measurements of visual brightness obtained from windows 28B and 26B, and 28C and 26C, respectively, after which the cycle of operation is repeated. As noted above, visual brightness values, and visual brightness difference, visual brightness contrast, and/or visibility calculations may be printed out at the printer 70 and/or displayed at the video monitor 22, as desired. Obviously, fewer or a greater number of targets may be employed. Also, in the illustrated operation, a single visual brightness measurement per television field of operation is provided. Obviously, a single measurement may be obtained over a period of several fields, or more than one measurement may be effected per field with modification of the circuitry to obtain and accommodate the plurality of brightness signals obtained by the use of a plurality of windows per television field.

Under conditions wherein a target is indistinguishable from the horizon sky background, visibility is known to be less than the distance to such target, and this information may be utilized by the computer. By use of targets at different ranges (at small azimuthal differences) improved accuracy in the calculation of visibility is possible. For example, only measurements obtained from visible targets at a maximum range from the camera may be used for visibility calculations to be outputted from the computer, if desired. It will be readily apparent that the use of a programmable digital computer in the monitoring system of this invention provides for extreme flexibility in the type of calculations which can be performed on the brightness measurements, and in the use of the results thereof.

Obviously, the visibility monitoring system is not limited to use of a fixed television camera for viewing a single scene. In FIG. 4, to which reference now is made, there is shown in fragmentary block diagram form a system which includes a pivotally mounted camera 16, which is mounted for movement about a vertical axis 80. A drive motor, such as stepper motor 82, is connected by mechanical linkage 84 to the camera for rotation thereof about axis 80 in the direction of arrow 86. The motor 82 is under computer 38 control for viewing the entire horizon. Targets, not shown, may be located at known distances from the camera about the entire horizon for visual brightness measurements by the system, from which measurements prevailing visibility readily may be calculated by use of the computer 38. Solution of equation (10), above, by the computer is involved in calculations of prevailing visibility.

Instead of a movable television camera, a plurality of stationary video cameras may be employed for viewing the entire horizon, as shown in FIG. 5 wherein cameras 16-1, 16-2, 16-3 and 16-4 are shown for viewing four horizon quadrants. A multiplexer 88 under digital computer 38 control may be used for sequentially switching from one camera output to another for making visual brightness measurements on targets, not shown, disposed about the entire horizon. Multiplexer control signals and window control signals for each target and associated horizon sky are simply programmed by use of the digital computer.

In the above-described visibility monitoring method and means, visual brightness measurements of substantially non-reflecting targets and associated adjacent horizon sky areas is shown since such measurements are involved in traditional visibility determinations. However, it will be apparent that brightness measurements may be made on adjacent targets of different reflectance, from which visibility may be determined, knowing the range to the targets. For example, adjacent low and high reflectance targets may be used. Consequently, as used herein, adjacent horizon sky may refer, as well, to an adjacent high reflectance target.

Also, it will be apparent that where horizon sky brightness measurements are employed, one such measurement may be used for making brightness contrast calculations relative to a plurality of substantially non-reflecting targets, if desired. That is, a single target or horizon sky brightness measurement may be paired with a plurality of other target brightness measurements to obtain brightness contrast values for the various other targets relative to the single target or horizon sky brightness measurements, if desired.

The invention having been described in detail in accordance with the requirements of the Patent Statutes, various other changes and modifications will suggest themselves to those skilled in this art, and it is intended that such changes and modifications shall fall within the spirit and scope of the invention as defined in the appended claims.

We claim:

1. In a visibility monitoring system, or the like, the combination comprising,
  video camera means for monitoring an area which includes at least first and second areas having different reflectivities,
  means responsive to the output from said video camera means for generating first and second digitized signals related to the visual birghtness of at least portions of said first and second areas, respectively, and
  means including a digital computer responsive to the digitized output from said means for generating said first and second digitized signals for computing a signal value related to said first and second digitized signals.

2. In a visibility monitoring system, or the like, as defined in claim 1 wherein said computed signal value is related to visual brightness contrast.

3. In a visibility monitoring system, or the like, as defined in claim 1 wherein said first and second areas comprise a substantially non-reflecting target and adjacent horizon sky, respectively.

4. In a visibility monitoring system, or the like, as defined in claim 3,
  wherein said computed signal value is related to visibility in the direction of the target and adjacent horizon sky.

5. In a visibility monitoring system, or the like, as defined in claim 3, which includes, at different distances from said video camera means, a plurality of substantially non-reflecting targets and associated adjacent horizon sky areas,
  means including said digital computer for control of said means for generating said first and second digitized signals such that first and second digitized signals related to visual brightness for each target and its associated adjacent horizon sky area are generated.

6. In a visibility monitoring system or the like, as defined in claim 5 wherein said digital computer is responsive to said first and second digitized signals for each of said targets and associated adjacent horizon sky areas for computation of a single signal value related to visibility in the direction of said targets.

7. In a visibility monitoring system, or the like, as defined in claim 3 wherein said means for generating said first and second digitized signals includes an integrator,
  analog-to-digital converter means responsive to the integrator output, and
  window generator means under control of said digital computer for control of said integrator for response thereof to video camera means output only at target and adjacent horizon sky areas within the viewing area of said video camera means.

8. In a visibility monitoring system, or the like, as defined in claim 3 including,
  means for moving said video camera means for viewing the entire horizon sky and adjacent substantially non-reflecting targets.

9. In a visibility monitoring system, or the like, as defined in claim 3 wherein said video camera means comprises a plurality of adjacent video cameras arranged to view substantially the entire horizon sky and substantially non-reflecting targets thereat.

10. In a visibility monitoring system, or the like, as defined in claim 9 wherein said digital computer is responsive to said digitized visual brightness signals for calculation of prevailing visibility.

11. In a method of monitoring visibility, or the like, the steps comprising,
  viewing by video camera means an outdoor area which includes at least first and second areas of different reflectivity, at least one of which first and second areas is at a known distance from the camera,
  from the video camera output, recurrently deriving digital signals related to brightness of at least portions of said first and second areas, and
  supplying said digital signals to a digital computer for use in calculating visual brightness contrast, visibility, or the like.

12. In a method of monitoring visibility, or the like, as defined in claim 11 wherein said one of said first and second areas which is at a known distance from the video camera means comprises a substantially non-reflecting target and the other of said first and second areas comprises an adjacent horizon sky area.

13. In a method of monitoring visibility as defined in claim 12 which includes viewing a plurality of non-reflecting targets located at known different distances from said video camera, and
  from the video camera output, recurrently deriving digital signals related to visual brightness for each of said targets and of adjacent horizon sky areas for use by said digital computer in calculating visibility.

14. In a method of monitoring visibility as defined in claim 13 including,
using said digital computer for calculating visibility from said known distances and said digital visible brightness related signals.

15. In a method of monitoring visibility as defined in claim 14 including,
using said digital computer to set window gates for control of the video camera output for viewing only said target and associated adjacent horizon sky areas for use in deriving said visual brightness related signals.

16. In a visibility monitoring system, or the like, the combination comprising,
at least one video camera for viewing a scene which includes at least one substantially non-reflecting target and adjacent horizon sky area,
a window generator responsive to horizontal and vertical synchronizing signals from said video camera for generation of window gating signals,
a digital computer for control of said window generator for positioning said window gating signals within the area of the target and adjacent horizon sky area, and
integrator means controlled by window gating signals from said window generator and responsive to the video signal from said video camera for generation of signals related to target and adjacent horizon sky visual brightness.

17. In a visibility monitoring system, or the like, as defined in claim 16 wherein,
said non-reflecting target is at a known distance from said video camera, and
said digital computer is responsive to the target and adjacent horizon sky visual brightness related signals for use in calculating visual brightness contrast, visibility in the direction of the target, or the like.

* * * * *